United States Patent [19]

Wilson

[11] 4,221,007
[45] Sep. 9, 1980

[54] METHOD FOR FITTING A STABILIZED ARTIFICIAL LIMB

[76] Inventor: Michael T. Wilson, 1259 Monument Blvd., Concord, Calif. 94520

[21] Appl. No.: 956,887

[22] Filed: Nov. 3, 1978

Related U.S. Application Data

[62] Division of Ser. No. 805,058, Jun. 9, 1977, Pat. No. 4,141,157.

[51] Int. Cl.³ .............................................. A61F 1/08
[52] U.S. Cl. ..................................... 3/21; 269/321 S; 269/321 W; 269/328; 269/53
[58] Field of Search ................................... 3/1, 2, 21; 269/322–328, 321 S, 321 W, 53, 55, 303, 307; 29/464, 466, 281.1, 281.4

[56] References Cited

U.S. PATENT DOCUMENTS 3,659,294  5/1972  Glabiszewski ............................ 3/21

FOREIGN PATENT DOCUMENTS 1274616  9/1961  France ............................................ 3/21
 535946  7/1977  U.S.S.R. ........................................ 3/21

*Primary Examiner*—Eugene H. Eickholt
*Attorney, Agent, or Firm*—Phillips, Moore, Weissenberger, Lempio & Majestic

[57] ABSTRACT

A method for fitting and stabilizing an artificial limb is disclosed herewith which includes the use of an adjustable prosthetic device to obtain dynamic alignment. After dynamic alignment, the relative orientation of the elements making up the adjustable limb are determined and transferred to the uniquely configured elements for stabilization of the entire limb by welding, brazing, or the like. The invention also includes the unique structure to practice the method.

16 Claims, 8 Drawing Figures

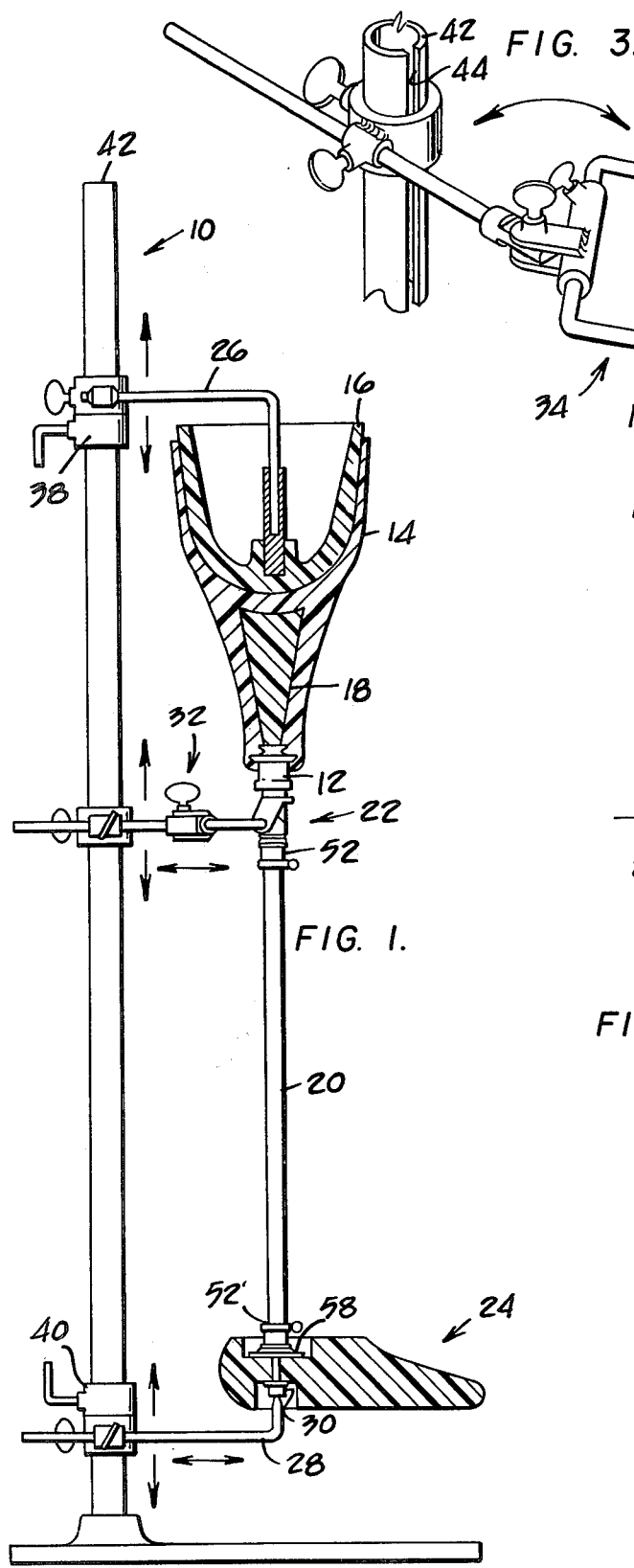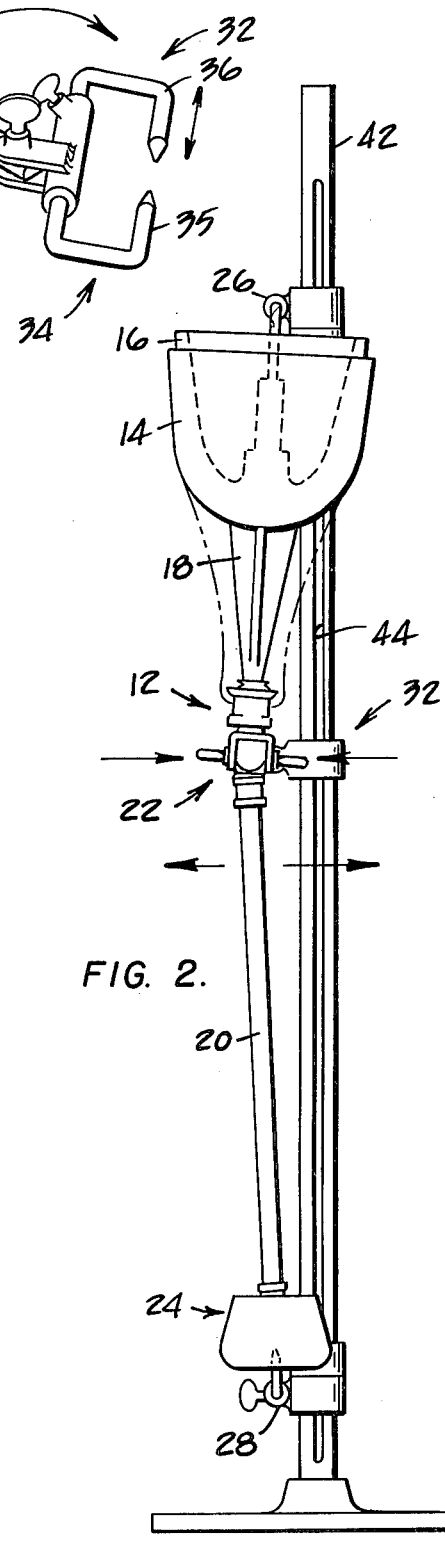

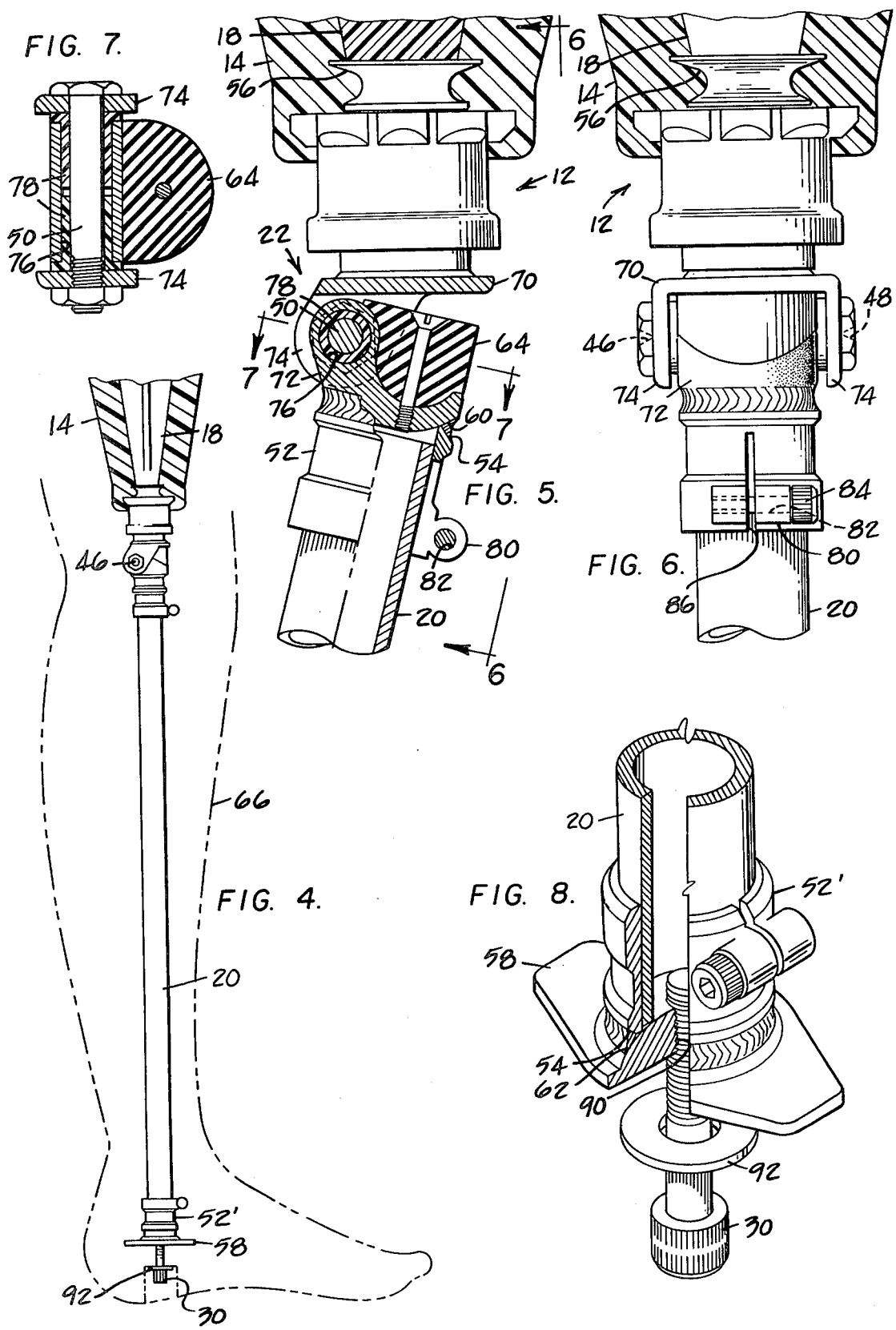

METHOD FOR FITTING A STABILIZED ARTIFICIAL LIMB

This is a division, of Ser. No. 805,058 now U.S. Pat. No. 4,141,157, filed June 9, 1977.

BACKGROUND OF THE INVENTION

This invention relates to the stabilization of artificial limbs.

Artificial limbs are generally fitted to patients by a skilled prosthetist utilizing components available in the art to make up the artificial limb. Until recently, artificial limbs were generally of the exoskeletal type, and where the artificial limb was to replace a leg removed above the knee, a complex knee joint was incorporated into the exoskeletal device, usually having some sort of a brake or release mechanism to allow flexing of the knee.

In recent years, the endoskeletal prosthetic device has been developed for use in replacing lower limbs, both in below-the-knee and above-the-knee amputations. An endoskeletal device more closely approximates the human structure in that the strength member usually includes a tubular structure approximating a human bone. By concentrating the strength member into a tubular skeletal-type prosthetic device considerable weight can be saved. Nevertheless, the uniqueness of each prosthetic device still requires individual fitting to the patient. Knee joints and bases to mount a prosthetic foot are currently available for use in such fitting. These devices incorporate adjustment features so that the individual prosthetic device may be fitted to the particular needs of the patient.

Although these adjustable prosthetic devices have proved very useful, they suffer from several drawbacks. First, adjustable fittings loosen after wear and must be reset to the measurements of the patient. Secondly, the adjustable elements may increase the weight of the entire prosthetic device, which is immediately reflected in patient fatigue. Furthermore, the increase in weight of a relatively long prosthetic device necessary in an amputation above the knee imposes a relatively large moment on the patient's relatively short stump. Accordingly, it is appropriate to reduce weight to a minimum in any prosthetic device without loss of strength.

Nevertheless, since each device must be uniquely tailored to the patient, the use of adjustable fittings for the attachment of pylons, the knee joint, and also what suffices to be an ankle joint, has become common. Unfortunately, such adjustable devices, even with their advantages over the old exoskeletal system, still suffer from aforedescribed drawbacks. In particular, the presently marketed adjustable devices will wear and the adjustments will become loose. Therefore, it becomes necessary for the patient to return to the prosthetist to have his prosthesis tightened and readjusted. With the loosening of the prosthesis, noise may be generated in the various joints which, although not critical to the operation of the device, can become embarassing to the user. In extreme cases, the prosthetic foot has been known to loosen to the point of coming off the prosthetic leg at an inopportune moment.

The development of the endoskeletal prosthesis was a great step forward in artificial limbs and the subsequent adjustability feature has been most helpful in obtaining proper fit. However, the adjustability feature is not needed once a satisfactory fit has been obtained. Fixing or stabilizing the rather expensive adjustable fittings is not economically sound, nor particularly sound from an engineering point of view. To weld the expensive adjustable fittings once a satisfactory fit has been obtained would not only be wasteful, but could add unnecessary weight to the prosthesis. Accordingly, a method has been devised and is disclosed herein to overcome the lasting disadvantages of the adjustable prosthesis while temporarily utilizing the adjustable prosthesis to obtain a satisfactory fit on a patient. Along with the method, particular structural elements have been invented to practice the invention.

SUMMARY OF THE INVENTION

This invention discloses a method for fitting a stabilized prosthetic device to an amputee. The prosthetic device includes a torque absorber, an interconnecting pylon, and a base adapted to receive a prosthetic foot. The method includes the steps of fitting dynamically an adjustable prosthetic device for use as a lower extremity to an amputee. The adjustable prosthetic device is then positioned relative a datum so that the orientation of the adjustable prosthetic device may be determined relative the datum. A base, an interconnecting plyon and a torque absorber are then positioned at the determined orientation of the adjustable prosthetic device relative the datum. Finally the pylon is fixed to the torque absorber and to the base in a permanent relationship.

Further, a unique link structure is disclosed which permits fixture of the various elements one to the other in a permanent fashion, such as by welding or brazing. This link structure includes a domed element and a beveled coupling which may be placed in an abutting relationship with the domed structure for permanent bonding thereto.

BRIEF DESCRIPTION OF THE DRAWINGS

FIG. 1 illustrates an endoskeletal prosthesis shown partly in section, mounted on a transfer device.

FIG. 2 shows the same endoskeletal prosthesis in a front elevation view.

FIG. 3 illustrates a clamp for holding the knee joint in the transfer device illustrated in FIGS. 1 and 2.

FIG. 4 is a side elevation view of a portion of the prosthesis shown in FIGS. 1 and 2, and illustrating the structure of the various elements.

FIG. 5 is a detailed view of an articulated knee joint in accord with the structure disclosed in the present invention.

FIG. 6 is the front elevation view of the same knee joint shown in FIG. 5.

FIG. 7 is a sectional view taken at line 7—7 of the knee joint illustrated in FIG. 5.

FIG. 8 is a perspective view of the base utilized for affixing a prosthetic foot to a prosthetic device.

DETAILED DESCRIPTION OF THE PREFERRED METHOD

The preferred method of performing this invention involves the use of an adjustable prosthetic device (not shown) and uniquely designed elements to make up a prosthetic device which are stabilized in accord with the following steps. The method will be described in the context of the uniquely described elements to be stabilized and in relation to FIGS. 1, 2 and 3.

In a lower limb amputation the method involves fitting a pylon to a prosthetic foot and to the socket in a particular relation unique to the amputee.

The method may also involve, in a lower limb amputation, fitting a pylon to a molded socket, an articulated knee to the pylon, a second pylon to the knee, and prosthetic foot to the second pylon. Such a device is shown ready for stabilization in FIGS. 1 and 2. However, before positioning the aforedescribed elements in the transfer device 10 of FIGS. 1 and 2, which serves as a reference or datum, the orientation of the amputee's prosthesis must first be determined by dynamically fitting a prosthesis to the amputee.

The process of fitting an adjustable prosthesis to an amputee is well known in the art and is not herein illustrated, but will be broadly described as a portion of the method. In every amputation of a lower limb, the amputee undergoes a period of adjustment to the artificial limb. Initially, the artificial limb is dimensioned by the experience of the prosthetist in relation to the remaining limb or to the information obtained before amputation or simply upon the experience of the prosthetist. With reference to the unique elements of FIGS. 1 and 2, such adjustment may require positioning of a torque absorber relative a socket which has been molded to fit the amputee's stump which is illustrated in FIG. 1 as a molded stump 16. Torque absorbers may be necessary for patients wherein trauma to the stump is a factor. The torque absorber allows rotation of the socket and hence the stump relative the prosthetic foot. During walking such rotation is normal so that without a torque absorber either the stump rotates in the socket or the foot rotates while engaged with the walking surface. The length of the prosthesis may be adjusted by appropriate cutting of an upper pylon and a lower pylon. The initial length adjustment is relatively easily determined from the height of the amputee based on his remaining good leg or, in the case of a double amputee, on the build of the individual.

The height adjustment of the upper pylon and lower pylon may, however, be changed as the positioning of the torque absorber, the adjustable knee joint, and the prosthetic foot are adjusted to the patient's needs. Such positioning is accomplished through the use of adjustable prosthetic devices which may include elements such as those disclosed in, for example, U.S. Pat. No. 3,659,294, issued to Richard Glabiszeweski, and other devices well known in the art.

Adjustment of the artificial prosthesis to fit a particular individual may take a period of several months and includes training sessions to insure the amputee is utilizing the prosthesis to its best advantage. Referring specifically to FIGS. 1 and 2, the prosthesis, when it is finally adjusted, may be placed in a transfer device such as transfer device 10.

It is to be understood that the prosthesis shown in FIGS. 1 and 2 is the prosthesis to be stabilized and is not the adjustable prosthesis just described. There are several critical positioning problems in fitting an artificial prosthesis. Initially, the appropriate torque absorber and the upper pylon in an adjustable prosthesis comparable to torque absorber 12 and pylon 18 in FIG. 1 are fitted to the patient based on the experience of the prosthetist. In the plane of the paper, as illustrated in FIG. 1, or the parasaggital plane of the patient, this positioning may be determined in part depending on the patient's age. Placing the comparable torque absorber 12 and pylon 18 in a more posterior position relative socket 14 than illustrated in FIG. 1 may be appropriate for a young, muscular type, while placing the torque absorber and the pylon in a more anterior orientation relative the socket would be appropriate for an elderly patient.

Most critical is the positioning of the articulating knee joint of the adjustable prosthesis comparable to articulating knee joint 22. It should be evident to those skilled in the art that it is a combination of the positioning of the knee joint and the prosthetic foot that determines the balance of the amputee. In FIG. 2 the position of knee joint 22 is an exaggerated "bow-legged" orientation to emphasize the flexibility required in fitting. In general, the center of gravity of the patient should be positioned comfortably over the center of the prosthetic foot. Once comfortable adjustment has been attained by the prosthetist using a temporary adjustable artificial limb, a process which may take several months, the adjustable artificial limb is placed in a datum such as transfer device 10.

The transfer device 10 serves as a jig to establish the orientation and position of each critical element of the adjustable prosthetic device relative the datum so that elements of the "to be stabilized" prosthetic device may be positioned in the device for stabilization. In particular, the stump 16, which has been molded from the patient, is positioned somewhat arbitrarily in an upper bracket 26, which is movable upwardly and downwardly relative the transfer device by means well known in the art. It should be understood the transfer device, such as illustrated here, is also well known in the art. The socket corresponding to socket 14 of the adjustable prosthetic device is then placed over the stump 16 so that the knee and foot subtend therefrom. The lower bracket 28, which has two degrees of freedom, is then positioned in a reference point of the adjustable prosthetic foot which has a counterpart reference point on the devices to be stabilized. This reference point may be a hexagonal socketed screw such as socket head screw 30 which is used in the device to be stabilized. Once the prosthetic foot of the adjustable prosthetic device is fixed in lower bracket 28, the central bracket 32 (see FIG. 3), which includes a bifurcated element 34, may be positioned about the axis of the knee joint of the adjustable prosthesis. It should be understood that central bracket 32 is movable vertically and laterally and also rotates. Bifurcated element 34 includes a fixed leg 35 and an adjustable leg 36, which is movable inwardly and outwardly of a reference point specifically the axis of rotation of the articulated knee joint, so that the position and axis of rotation of the knee joint may be determined relative the datum. It can be seen, at this point, that having positioned the adjustable artificial limb in the transfer device 10, the position of the prosthetic foot relative the datum has been established. Furthermore, the position of the articulated knee joint has also been established relative the prosthetic foot of the adjustable prosthetic device and also relative the socket of the adjustable prosthetic device.

Once these positions have been established as indicated above, the adjustable prosthetic device is removed from the transfer device 10 by relieving bifurcated leg 36 without disturbing the relationship of the bifurcated element 34 relative the datum. Secondly, the upper bracket 26 and the lower bracket 28 may be moved away from the central bracket 32 after a stop member 38 for the upper bracket and a stop member 40 for the lower bracket 28 are positioned against the brackets. Upper bracket 26 and lower bracket 28 may be prevented from rotation about the vertical member 42 of transfer device 10 by a slot or groove 44 which runs longitudinally in the upright member 42 and in which a tongue of the upper and lower brackets will travel.

Once the adjustable limb is removed from the transfer device, the transfer device then becomes a jig to build up the elements of the "to be stabilized" prosthesis. Initially, the knee joint 22, which may be fitted with a torque absorber 12 is positioned in the central bracket 32. (Reference should be made to FIG. 6, wherein a knee joint appropriate for use in this method is shown in detail.) It will be noted that knee joint 22 shown in FIG. 6 has indentation 46 and 48 in either end of the axis of rotation of the knee joint formed by a bolt member 50 (see FIG. 7). With knee joint 22 in position in central bracket 32, upper pylon 18 which may be of rigid plastic foam may be positioned relative the stump mold 16, knee joint 22 and the affixed torque absorber 12, which itself is the subject of co-pending application Ser. No. 805,059, now U.S. Pat. No. 4,134,159 issued Jan. 16, 1979 to Micheal T. Wilson. Uper pylon 18 may be affixed to flange 56 of torque absorber 12 (or to a similar flange integrally formed with knee joint 22 when a torque absorber is contra-indicated) by an epoxy adhesive or the like.

Socket 14, after lowering of the bracket 26 and stump mold 16 to the previously determined position, may be then molded about torque absorber 12, upper pylon 18 and stump mold 16 in a manner well known in the art using a medium such as glass fibers and bonding agents or the like. It has been found helpful to use a partial vacuum in introducing a bonding agent to a flexible mold in forming socket 14.

Lower pylon 20 may then be placed in position between knee 22 and the prosthetic foot 24 which is fitted with a base 58 (see FIG. 8). Placed at either end of pylon 20 are couplings 52 at the upper end and 52' at the lower end. Couplings 52 and 52' may be identical, and each will have a beveled surface 54 (see FIGS. 5 and 8). The beveled surface 54 of coupling 52 may be placed in an abutting relationship with a domed surface 60 on the lower portion of knee joint 22. Similarly, the beveled surface 54 of coupling 52' may be placed in an abutting relationship with a domed surface 62 formed on base 58. It is to be understood that lower bracket 28 is returned to the determined position found in the earlier step from the adjustable leg.

In one type of structure envisioned for use in this method of fitting a stabilized artificial prosthesis, certain inflammable elements should be removed from the knee joint and the foot prior to bonding of the surface together. For example, the resilient member 64, located in knee joint 22, should be removed and replaced with a non-flammable spacer during the bonding process. Similarly, the prosthetic foot 24 may also have to be removed, depending upon the flammability of the foot. It should be noted that socket head screw 30 may be extended to its normal position once the prosthetic foot 24 is removed from the transfer device 10, which is the datum. With the flammable members removed from knee joint 22 and from prosthetic foot 24, the beveled surfaces 54 may be bonded to the domed surfaces 60 and 62 respectively by welding, brazing, or the like.

Once the bonding process is complete, the various flammable members removed before bonding may be replaced, and construction of the cosmetic surfaces of the artificial leg denoted by the dashed lines 66 in FIG. 4 may be constructed in a manner well known in the art.

Although subsequent adjustment has not proved necessary in use of this particular device, adjustment could be accomplished by removal of the cosmetic surface 60.

It will be understood by those skilled in the art that a below-the-knee prosthesis stabilization would follow from the above description by eliminating the knee joint. In such a prosthesis the torque absorber 12 if used would be fitted with a clamp similar to coupling 52 for fixture to pylon 20. The fitting of the foot would follow using the structure shown in FIG. 8. The torque absorber would then be molded to the stump mold 16.

The Unique Structure

Although it should be apparent to those in the art what the particulars of the unique structure herein disclosed are at this point following the discussion of the method, a detailed description of the structure follows.

In particular, this invention envisions a domed surface formed on one element which may replace a joint such as a knee or ankle as shown in FIGS. 5 and 8 and used in conjunction with the beveled surface formed on a second element such as beveled surface 54 found on representative coupling 52 the two forming a link for interconnecting two parts of a prosthesis.

Referring specifically to FIGS. 5 and 6, it will be seen that articulating knee joint 22 is formed with a first portion 70 which may be adapted to have permanently affixed thereto a torque absorber 12 and a second portion 72 fixable to the lower pylon 20 by coupling 52. It should be understood that upper portion 70 may be affixed directly to pylon 18 by means such as epoxy type adhesive if a torque absorber 12 is contra-indicated. In this case the knee joint 22 would be formed with an integrally formed flange in the manner of flange 56 of torque absorber 12 so that socket 14 could be formed thereabout. A simple expedient in manufacturing is to form all knee joints 22 with a flange which may be removed to allow bonding of the torque absorber. First portion 70 has subtending a bifurcated structure 74 through which axle 50 of the articulated joint passes. Similarly, the second portion 72 is bored as at 76 to receive bushing means such as bushing 78 which may be of a plastic polymer material well known in the art and which serves as a permanent bearing. Affixed to second portion 72 is the resilient member 64 by a bolt 65 or the like. Resilient member 64 is disposed between the first portion 70 and the second portion 72 to form the mating surface with the first portion 70. Resilient member 64 may be of an elastomer or the like to provide means for absorbing a certain degree of shock as the articulation closes. It will be understood by those familiar with the art that as the artificial limb is used, the motion of the amputee in swinging the artificial leg forward will close the articulated joint so that resilient member 64 will come in contact with the first portion 70 in the manner of a locking knee.

One of the important features of the knee joint 22 is the domed surface 60, to which a representative coupling 52 may be affixed. Coupling 52 is generally a hollow cylinder and is formed with a hollow frustoconical end thereby defining a beveled surface 54 to form an appropriate joint with the domed surface of the mating element to which the coupling 52 may be welded or brazed. At the other end of coupling 52, a tangential boss 80 may be formed having a bore 82 therethrough (see FIG. 6) in which an adjusting bolt 84 may be threadably engaged. An axially aligned slot 86 may be formed through the boss 80 and a coupling 52 so that tightening of bolt 84 which may be socket headed, causes the coupling 52 to act as a clamp on the tubular pylon 20, thus fixing the coupling 52 to the pylon 20 to form skeletal pylon means to interconnect a knee with a foot. It should be noted that only one portion of the bore 82 formed in boss 80 may be threaded, with the other portion being of a diameter sufficient to receive bolt 84 without engagement of the threads.

Referring to FIG. 8, it can be seen that the base 58 is formed, in the manner previously described for a knee 22, with a domed head 62. In particular, base 58 is an elongated plate member with the dome 62 extending outwardly from one side thereof. A threaded bore 90 is formed in the center of dome 62 to threadably receive screw 30 which may have a socket head. A washer 92 may be disposed between the head of screw 30 and the prosthetic foot 24 molded to fit on base 58.

Operation of the structure herein described should be evident from the method previously described; however, in review, the beveled surface 54 of a representative coupling is placed in an abutting relationship with a domed surface of the knee joint or the base plate as appropriate and in the angular relationship determined by the dynamic alignment of the adjustable prosthetic device. Once the beveled end is in this relationship and held there with the transfer device 10 forming a datum, the beveled end 54 is bonded with the domed surface by welding, brazing, or the like.

The combination of the dome and bevel as described herein allows the elements of the prosthesis to be positioned in various angular orientations while retaining the V-joint appropriate for proper metallic bonding.

Although this invention has been described in relation to a particular method and a unique structure, it is to be understood that variations within the skill of the art are to be considered within the purview of this description.

The embodiments of the invention in which an exclusive property or privilege is claimed are defined as follows:

1. A method for fitting a stabilized prosthetic lower extremity including a torque absorber, an interconnecting pylon, and a base adapted to receive a prosthetic foot to an amputee comprising the steps of:
    fitting dynamically an adjustable prosthetic lower extremity to the amputee;
    removing the adjustable prosthetic lower extremity from the amputee;
    positioning the adjustable prosthetic lower extremity relative a datum;
    determining the orientation of the adjustable prosthetic lower extremity relative the datum;
    removing the adjustable prosthetic lower extremity from the datum;
    positioning the base, the torque absorber, and the interconnecting pylon at the determined orientation of the adjustable prosthetic lower extremity relative the datum so that the elements to be stabilized are oriented in the same relation as the adjustable prosthetic lower extremity;
    fixing the pylon, the torque absorber, and the base in a permanent relationship.

2. The method of claim 1 wherein the step of fixing the pylon to the base is accomplished by welding.

3. The method of claim 1 wherein the step of fixing the pylon to the base is accomplished by brazing.

4. The method set forth in claim 1 further including the step of fitting a prosthetic foot to the base following the step of fixing.

5. The method set forth in claim 4 including the step of fitting a cosmetic outer surface to the pylon and torque absorber following the step of fitting the prosthetic foot.

6. The method of claim 5 wherein the positioning step includes positioning an articulated knee having the torque absorber affixed thereto.

7. The method of claim 6 wherein the step of fixing the pylon to the base includes fixing the pylon at the other end to the articulated knee.

8. The method of claim 7 wherein the articulated knee includes inflammable elements and the method further including the steps of removing inflammable elements from the knee before the step of fixing, and following the step of fixing, replacing the inflammable elements.

9. The method of claim 8 wherein the step of fixing is accomplished by welding.

10. The method of claim 8 wherein the step of fixing is accomplished by brazing.

11. A method for fitting an amputee with a stabilized prosthetic lower extremity including as elements thereof an upper pylon, a lower pylon, a base for receiving a prosthetic foot, and an articulating knee joint comprising the steps of:
    fitting dynamically an adjustable prosthetic lower extremity including an adjustable prosthetic socket, an adjustable prosthetic base for receiving a prosthetic foot, and an adjustable prosthetic knee on the amputee;
    removing the adjustable prosthetic lower extremity from the amputee;
    determining the position of the adjustable prosthetic lower extremity relative a datum;
    removing the adjustable prosthetic lower extremity from the datum;
    transferring the determined position of the adjustable prosthetic lower extremity to the elements of the prosthetic lower extremity to be stabilized;
    fixing the elements of the prosthetic lower extremity to be stabilized in a permanent relationship.

12. The method set forth in claim 11 wherein the step of determining the position of the adjustable prosthetic device includes the following steps:
    positioning of the adjustable prosthetic socket relative the datum;
    determining the position of the adjustable prosthetic foot relative the datum;
    determining the position of the adjustable prosthetic knee relative the datum, the adjustable prosthetic foot, and the adjustable prosthetic socket.

13. The method set forth in claim 12 wherein the step of transferring the determined alignment of the adjustable prosthetic device includes the steps of:
    transferring the determined alignment of the adjustable prosthetic base relative the datum to the stabilized prosthetic base;
    transferring the determined alignment of the adjustable prosthetic knee relative the datum to the stabilized prosthetic knee; and
    positioning the upper pylon relative the datum and the adjustable prosthetic knee to allow formation of a stabilized socket.

14. The method of claim 13 wherein the step the elements of the stabilized prosthetic device includes the step of:
   interconnecting the stabilized prosthetic knee to the stabilized prosthetic base by use of the lower pylon.

15. The method of claim 14 wherein the step of fixing the prosthetic knee to the prosthetic base by the use of the lower pylon is accomplished by welding.

16. The method of claim 14 wherein the step of fixing the prosthetic knee to the prosthetic base by the use of the lower pylon is accomplished by brazing.

* * * * *

UNITED STATES PATENT AND TRADEMARK OFFICE
CERTIFICATE OF CORRECTION

PATENT NO. : 4,221,007
DATED : September 9, 1980
INVENTOR(S) : Michael Thomas Wilson It is certified that error appears in the above—identified patent and that said Letters Patent is hereby corrected as shown below:

Column 2, line 24, change "plyon" to --pylon--.
Column 5, line 20, change "Micheal" to --Michael--.
Column 9, line 1, between "step" and "the" insert --fixing--.

Signed and Sealed this

Sixteenth Day of December 1980

[SEAL]

*Attest:*

*Attesting Officer*

SIDNEY A. DIAMOND

*Commissioner of Patents and Trademarks*